United States Patent [19]

Bischof et al.

[11] 4,228,089
[45] Oct. 14, 1980

[54] METHOD AND APPARATUS FOR FRACTIONAL CRYSTALLIZATION SEPARATION

[75] Inventors: Rudolf Bischof, Sevelen; Heinz Rhyner; Kurt Saxer, both of Buchs, all of Switzerland

[73] Assignee: Metallwerk AG Buchs, Buchs, Switzerland

[21] Appl. No.: 908,986

[22] Filed: May 24, 1978

[30] Foreign Application Priority Data

May 31, 1977 [CH] Switzerland .......................... 6639/77
Apr. 24, 1978 [CH] Switzerland .......................... 4367/78

[51] Int. Cl.³ .......................... C09F 5/10; C11B 3/00; B01D 35/18
[52] U.S. Cl. .......................... 260/428.5; 260/412.8; 260/419; 62/532; 62/537; 62/541; 210/175; 210/177; 210/181; 210/184; 210/187
[58] Field of Search ............. 260/428.5, 412.8, 419; 62/532, 537, 541; 210/175, 177, 181, 184, 187

[56] References Cited

U.S. PATENT DOCUMENTS 2,576,841  11/1951  Leaders et al. .................... 260/428.5
3,621,664  11/1971  Saxer ........................................ 62/58

*Primary Examiner*—John F. Niebling
*Attorney, Agent, or Firm*—Frishauf, Holtz, Goodman & Woodward

[57] ABSTRACT

A method for separating components of a substance, for example, a fatty acid ester such as palm oil, by dissolving the substance in a solvent. The resultant solution is circulated and cooled in a circuit with crystals being formed in the solution as the temperature is lowered. The crystals are continuously separated from the circulating solution during the crystal separation phase of the process. The crystals are then preferably washed and recovered. Preferably there is a second crystallization phase in the process. The invention includes the apparatus used to carry out the process and, particularly, novel fractionating columns and filter surfaces within said columns used in the preferred embodiments of the process.

33 Claims, 4 Drawing Figures

METHOD AND APPARATUS FOR FRACTIONAL CRYSTALLIZATION SEPARATION

BACKGROUND OF THE INVENTION

The invention refers to a method for fractionation of substances by crystallization in which the raw product, particularly a mixture of fatty acid esters, is mixed with a solvent and the solution obtained thereby is circulated in a circuit with crystals being formed in the solution by gradually lowering the temperature.

The method is particularly suitable for fractionation of mixtures of fatty acid esters and other slowly crystallizing mixtures of substances and/or mixtures of substances difficult to filtrate. Natural fats or oils are mixtures of mono-, di- and triglycerides of saturated and unsaturated fatty acids. For their further use the problem occurs to fractionate the natural raw product into two or more fractions having melting points differing considerably from each other; e.g. into fat and oil fractions. The part with the highest melting point is often not suitable for use in foodstuff, but is only usable for industrial purposes. For reasons of economy this fraction should be separated in highly concentrated form.

Normal palm oil has a melting point of approximately 40° C. (Celsius). To obtain with a good yield an oil fraction with a melting point lower than 10° C. is a problem which is not yet solved satisfactorily for bulk processing.

A similar fractionating problem is posed after glycerides have been transformed by ester interchange into methyl fatty acid esters or other esters.

In food technology, and in chemical technology fractionation of mixtures of substances by employing the different crystallization temperatures of the components is a generally employed method. This method is gentle from the point of view of operating temperatures and offers in many cases substantial advantages compared to other possible methods, e.g. distillation. For the fractionation of mixtures of chemically similar substances, crystallization is very often the preferred fractionating method for reasons of its economy. This is also true for the fractionation of mixtures of fatty acid esters. However, in this case the use of crystallization is particularly difficult, because the components capable of crystallization tend strongly to undercooling and after initiation of crystallization form crystal mixtures with low selectivity. Further, the separation of the crystals from the liquid phase with known means such as sedimentation or filtration is expensive and of low selectivity. By adding a solvent the conditions can be slightly improved, but the basic problems remain. The use of crystallization causes additional problems when the substance to be crystallized may form different crystal modifications on lowering of the temperature.

In a known method for separating of mixtures of glycerides of fatty acids, the so-called winterizing method, the raw product is slowly cooled in tanks and stored for a long period of time at the end temperature. A crystal fraction is formed at the bottom of the tank, and in the other portion of the tank a liquid oil fraction is formed. These fractions are then separated by decanting. This method is time consuming and, because of lacking selectivity, not very advantageous with respect to yield.

In another known method, the raw product is mixed with a solvent in high excess and then slowly cooled in an agitator vessel or in a scraper crystallizer. After reaching the end temperature, the crystals are separated from the liquid phase in centrifuges or filters, and by washing the crystals with fresh cool solvent the selectivity is increased. For fractionation of palm oil according to this method acetone or methyl-ethyl-ketone (MEK) is used as solvent. However, it has been found that it is very difficult to obtain low melting oil fractions according to this method. In addition, the use of mechanical means in forming and separating the crystals is very expensive and not very reliable.

It is an object of the present invention to provide a method which does not have the disadvantages of the prior art methods. According to the invention, a method for fractionation of substances by crystallization is provided, said method comprising mixing the raw product, in particular a mixture of fatty acid esters, with a solvent and circulating and cooling the solution in a circuit, with crystals being formed in the solution by gradually lowering the temperature, and characterized in that the crystals are continuously separated from the circulated solution.

The invention also refers to a device for carrying out the method, said device comprising in the circuit a circulation pump, a cooler/heater and a storage tank, and is characterized in that a fractionating column is further provided in the circuit.

The invention relates also to the use of the method for fractionation of mixtures of fatty acid esters, particularly mixtures of glycerides.

It has been found that fractionating of fatty acid esters by crystallisation is particularly effective when the raw product is mixed with a solvent of the alkane sequence, preferably hexane (alkane $C_6$) and is slowly cooled, the crystals formed during cooling being continuously separated from the liquid phase.

Further, it has been found that this method is particularly easy when the fatty acid ester/solvent mixture is pumped in a circuit through a cooler and a fractionating column. By controlled cooling crystallization takes place, and in the fractionating column the crystals are continuously removed from the circuit.

It has been found that the fractionating column operates particularly effectively when the solution containing the crystals trickles on slightly inclined filter surfaces connected for cross-current and covered with a felt of synthetic fibres. The crystals are kept on the filter surfaces, whereas the solution freed from the crystals drops through and can be collected at the bottom of the column. The filter surfaces are progressively filled and covered with crystals from the top to the bottom. When the upper filter surfaces are filled, the solution containing the crystals are fed in cross-current over these filter surfaces to the lower filter surfaces still being active. These filter surfaces are finally also covered with crystals.

It has been found that after reaching the end temperature corresponding to the desired fractionation the circuit can be interrupted and the oil/solvent fraction can be drawn off. By circulating fresh solvent and cooling at the same temperature the crystal fraction in the fractionating column can be washed effectively one or several times. The collected washing solution can be withdrawn after each washing and be added to the oil fraction or employed as solvent for the raw product or initial product on the next fractionation.

The crystals remaining in the fractionating column can be removed in molten form after adding solvent and circulating the solvent under heat supply.

An embodiment of the invention will now be described with reference to the drawing.

Figure 1:
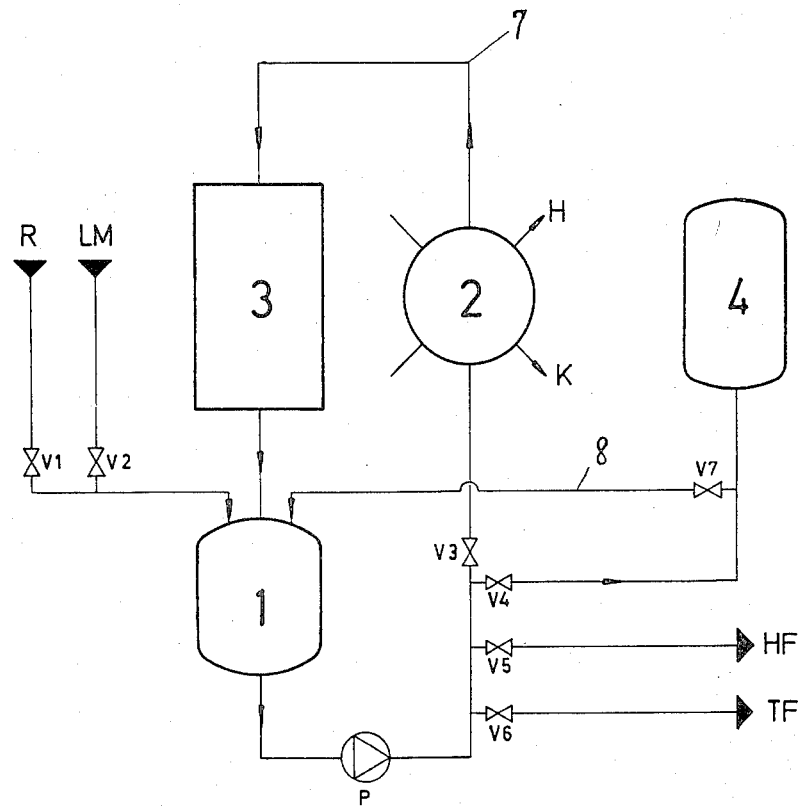
FIG. 1 illustrates a flow sheet including apparatus for fractionating in accordance with the present invention.

The apparatus shown in FIG. 1 comprises essentially a storage tank 1, a pump P, a cooler/heater 2, and a fractionating column 3 connected together to form a circuit. In this circuit the valve $V_3$ is provided. One or more tanks 4 are provided to contain intermediate fractions. The connection of the circuit 7 to the tank 4 may be made through valve $V_4$. If desired, the content of the intermediary tank 4 can be fed through valve $V_7$ and the duct 8 leading to the storage tank 1 back to the circuit 7. The feeding of the raw product R and the solvent LM to the circuit takes place through valves $V_1$ and $V_2$, respectively. The high melting fraction HF and the low melting fraction TF can be withdrawn through valve $V_5$ and the valve $V_6$, respectively.

Figure 2:
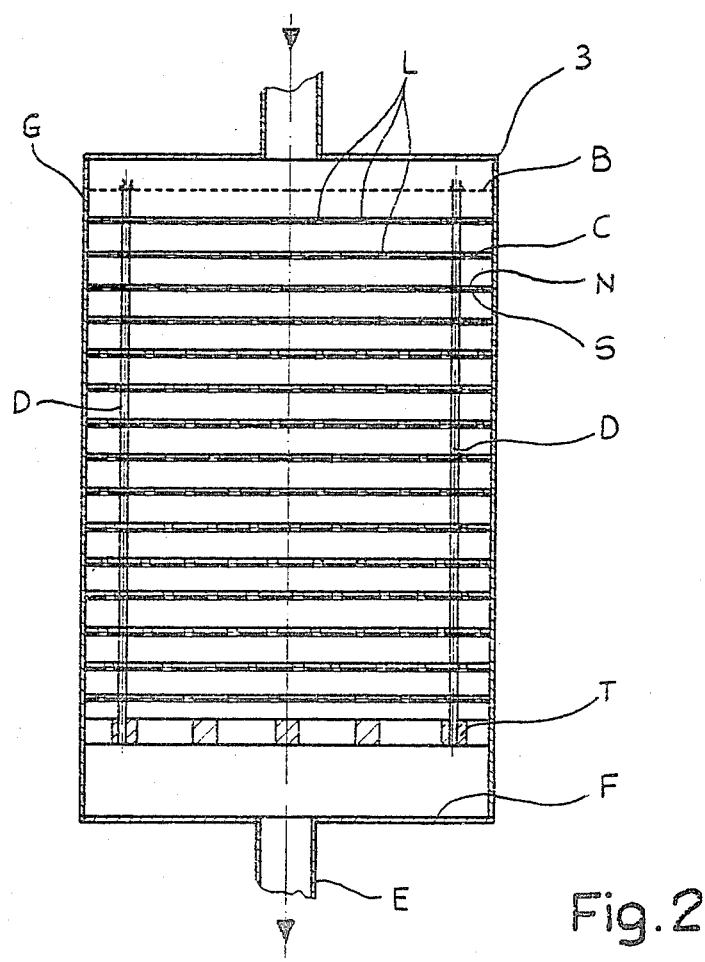
FIG. 2 is an embodiment of a fractionating column in cross-section, useful as part of the apparatus according to FIG. 1.

Before describing the method in detail it is advisable to consider first the structure of the fractionating column 3. A preferred embodiment of the fractionating column is shown in FIG. 2. It comprises preferably a vertical cylindrical housing G. A distributor plate B, which may be a perforated sheet, is located at the top. This permits an even sprinkling of the column cross-section.

Located in the fractionating column are horizontal filter surfaces C provided with spaced holes L through which liquid flowing through or over the filter material can drop on the next lower filter surface C. The holes L of adjacent filter surfaces are off-set with respect to each other, so that the liquid must always travel in horizontal direction on the filter surface C before it can drop through holes L to a lower filter surface C. The filter surfaces C are preferably mounted on at least two spacers D located at a distance from each other. The filter surfaces C form together with the perforated sheet B a unit which can be inserted or removed from the column. The spacers D are formed by tubes extending somewhat above the distributor plate B. Accordingly, these tubes form a connection between the top and the bottom of the column and permit aeration. Normally no liquid is flowing through tubes D. However, if for any reasons the perforated plate B should be jammed, the liquid could flow through the tubes D so that no impermissible excess pressure is created in the column. The tubes D are supported on a support frame T.

Figure 3:
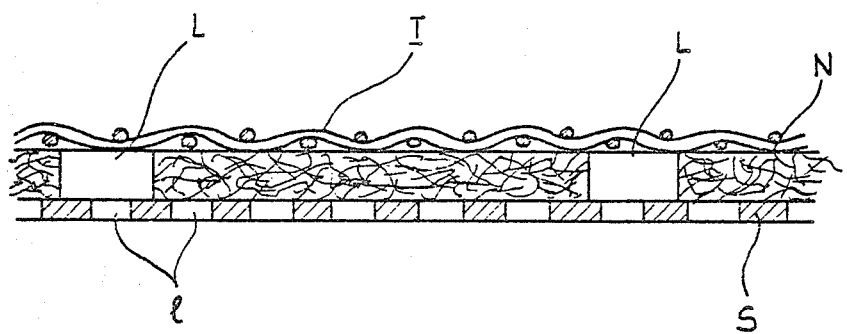
FIG. 3 is in enlarged scale a preferred embodiment in cross-section of the perforated plate S and the filter C of a fractionating column.

As illustrated in FIG. 3, each filter surface C has a support structure with a flat sieve or perforated plate surface S on which the filter material is located. The filter material consists preferably of felt. The material and the structure of the felt can be closely adapted to the fractionating problem. Polypropylene or polyester proved to be a suitable material for glycerides. The preferable thickness of the felt is situated between 5 and 10 mm. The diameter of the pores is preferably approximately 50 micron.

Even if it is possible to design the filter C and the perforated sheet S in such a way, that the holes provided therein register accurately, the embodiment shown in FIG. 3 is more advantageous. There, the perforated sheet S comprises distributed over its whole surface a plurality of closely spaced small holes 1 of approximately 4 mm diameter. The filter C comprises fewer but larger holes L of approximately 10 mm diameter distributed in larger spacings, for example 50 mm over the whole surface. In this way, on mounting of the filter C on the perforated sheet S there will always be ports for the liquid. Instead of a perforated sheet it is also possible to use a sieve. To prevent a possible buckling of the felt it is advisable to put over the felt a wire mesh I.

On crystallization the described construction of fractionating column provides for equal deposits on the filter surfaces from the top to the bottom of the column without causing backing up of liquid. The formed fine crystals stick to the fibres of the felt. The remaining liquid flows through or over the felt to the holes L or l and drops onto the next lower filter surface C. The same takes place on the other filter surfaces C. In this construction a relatively small amount of liquid travels a relatively short distance at low flowing velocities. In other words, the so-called hold-up of the column is small. An even deposition takes place on all filter surfaces C. There will be no irregularities on the filter surfaces which could canalize the liquid. This is of particular importance on a washing operation, because then all filter surfaces will be wetted and cleaned by the liquid.

Figure 4:
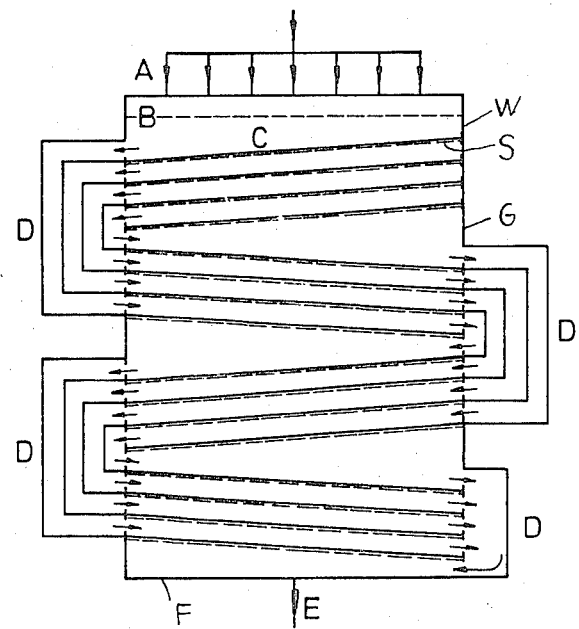
FIG. 4 is a further embodiment of a fractionating column in cross-section.

Another embodiment of the fractionating column 3 is shown in FIG. 4. In this embodiment the fractionating column 3 comprises preferably a housing G defined by vertical or slightly inward inclining walls W. A distributor plate B is provided at the top. The distributor plate B may be a perforated sheet to which distributing ducts A are leading. This provides for sprinkling of the column cross-section.

In the fractionating column there are filter surfaces C slightly inclined with respect to the horizontal plane. The filter surfaces C are individually or in groups connected by reversing means D. The down flowing solution can collect at the bottom F of the fractionating column 3 and flow away through the output duct E.

Each filter surface C comprises a support structure having a flat sieve surface or perforated sheet surface S on which the filter material is located. The filter material consists preferably of a felt and is advantageously connected to the perforated sheet S at a plurality of spots.

The material and the structure of the felt may be substantially adapted to the stated fractionating problem. Polypropylene or polyester proved to be a suitable material for glycerides. The fine crystals stick on the fibres of these materials. The preferable thickness of the felt is situated between 5 and 10 mm. The diameter of the pores is preferably approximately 50 microns.

On crystallization the described construction of the fractionating column 3 provides for equal deposits on the filter surfaces from the top to the bottom without causing backing up of liquid. After crystallization, the remaining liquid drains rapidly and practically completely. On washing and on melting of the crystals all filter surfaces are again wetted by the liquid. The shown construction permits that on melting all crystals get into contact with the warm liquid and are completely molten and removed.

After this description of the apparatus and its functions the method described below will be easily understood. Also the advantages of the method will be easily seen.

At the beginning of the method the initial product, in the present case palm oil and the solvent are fed into the circuit. By a short time cooling to about 15° C. under the liquidus point of the solution crystallization is initiated, whereupon the temperature is again increased by about 10° C. Relatively large crystals are formed, which are soon retained in the fractionating column 3. Then the solution circulating in the circuit becomes clear. Now, by cooling with the cooler/heater 2 the temperature of the solution circulating in the circuit is linearly with time lowered until the end temperature corresponding to the desired fractionation is attained. During this time the solution remains practically clear, which means that the undercooling of the solution is continuously reduced by the forming and growing of crystals in the column.

After shutting-off of the circulation pump P and dripping off of the remaining solution from the fractionating column 3 the cooled solution is pumped from the storage tank 1 as low melting fraction TF through the duct provided with the valve $V_6$.

After feeding of fresh solvent through the valve $V_2$, the solvent is pumped under further cooling, which causes the crystals contained in the fractionating column 3 to be washed. The washing solution can also be pumped off as low melting fraction TF. Preferably, then again one or two further similar washing operations are carried out, but the washing solution is then pumped into the intermediary tank 4.

After feeding a further amount of solvent the solvent is circulated under heating. This causes the crystals contained in the fractionating column 3 to be molten and to be brought into solution. This solution can be pumped off as high melting fraction HF. With a further amount of solvent the rest of the high melting fraction is removed from the fractionating column and from the circuit 7.

Now a further operating cycle may take place by feeding the initial product through valve $V_1$ into the circuit 7. In this case, however, the solvent which has been used on the washing operation and stored in tank 4 is employed by opening valve $V_7$. If necessary, fresh solvent may be added through the valve $V_2$.

It may be mentioned that the solvent contained in the low melting and in the high melting fraction is again recovered by distillation, whereupon it can be used again. After distillation the end products are present in the desired form.

The described method may be modified in different ways. For example, it is possible on the separation in two fractions to adapt the number of washing operations and the distribution of the solutions after washing according to the fractionating problem.

In the apparatus shown in FIG. 1 it is also possible to carry out a fractionation into three or more fractions. As already described, a first high melting fraction is separated. The rest and a part of the washing solutions are then subjected to a second fractionation whereby a low melting fraction is obtained as liquid and an intermediate-melting fraction as crystals. The same fractionation could also be obtained by two apparatus according to FIG. 1 connected in series.

Also the construction of the separating column 3 is not limited to the described flow of the liquid in cross-current. The filter surfaces may also be arranged in the form of one or more parallel running archimedic screws with vertical axes.

Compared to the usual methods the described method has a large number of advantages, which make it particularly interesting for use on fatty acid glycerides. On fractionating of fatty acid glycerides which is generally considered as difficult, a large difference in melting points of the fractions is obtained which leads to a good yield. The use of solvents from the alkane sequence, in particular of hexane, is safe in foodstuff technology.

Also from the view of energetics, the use of these solvents is interesting, because of the low heat of evaporation. Compared with conventional methods using solvents the required amount of solvents is substantially smaller. The method is very flexible with respect to changes of requirements concerning the fractionation. Of particular interest is that no special mechanical moving elements are required with exception of the pump and the valves.

A practical example of the operating characteristics of the method shall be illustrated. It should be pointed out, that there is no intention to limit herewith in any way the field of application of the invention.

EXAMPLE

The following example has been carried out with an apparatus according to FIG. 1. The fractionating column 3 contained ten round filter surfaces of 180 mm diameter. On the side of the liquid the filter surfaces were individually connected together for cross-current. The felt had a thickness of 8 mm and a porediameter of 50 micron. The pump was rated for 200 liters per hour. 1600 gramm raw palmoil with a melting point of 40° C. were mixed with 2800 g hexane and circulated. Initiation of crystallization took place at +10° C., whereupon the apparatus was brought to +20° C. After five minutes the solution was clear. Now, the temperature has been brought during 30 minutes linearly to −15° C., whereupon the liquid phase was withdrawn (2300 g). After three washing operations at −15° C. the crystal fraction was removed.

Afterwards the liquid phase and the washing solution of the first fractionation were combined and the hexane was partly evaporated. The rest consisted of 1320 g depleted palm oil and 3000 g hexane. In a second crystallization operation the temperature lowered during 30 minutes from −15° C. to −24° C. After removal of 3200 g liquid rest one washing was made at the end temperature with 1400 g hexane. The liquid rest and the washing solution were combined. Under heating the remaining crystals were subsequently removed with hexane.

After fractionation and evaporation of the solvent the following solventfree amounts were measured:

| | | |
|---|---|---|
| First crystallization | 280 g | melting point 52° C. |
| Second crystallization | 590 g | melting point 28° C. |
| Liquid phase | 730 g | melting point approx. 5° C. |

The fatty acid esters which are preferably used in the process of the present invention are those in which the fatty acid residue comprises at least one fatty acid having from 12 to 20 carbon atoms. The fatty acid may be saturated or unsaturated, or as is often the case in naturally occuring fatty acids, a mixture of both. The alcohol component of the fatty acid esters may preferably be glycerine, methyl alcohol or alcohols with aliphatic chains of two to six carbon atoms.

The solvents which are preferably used in this process are alkanes liquid at the operating temperature and pressure. Depending on the solubility of the raw material, another solvent may be used such as toluene, xylene, benzene or other aromatic solvents, acetic acid, dimethyl formamide, dimethyl sulphoxide, acetone, methyl-ethyl-ketone.

By the term crosscurrent flow used in this specification it is understood that the liquid, as far as it flows on the filter surfaces, is moving in a zig-zag fashion through the column.

We claim:

1. A method for fractionation of a mixture of fatty acid esters materials dissolved in a solvent, said method comprising circulating and cooling the solution in a circuit,
    said circuit comprising a circulating pump, a cooler, a heater, a storage tank and a fractionation column,
    said fractionation column further comprising at least one filter surface,
    stage (1) lowering the temperature gradually, causing formation of crystals suspended within said solution, said crystals forming while totally suspended within the solution, and continuously separating the crystals from the circulating solution by passing the crystal-containing solution in contact with said at least one filter surface whereby crystals are collected on said at least one crystal surface and then recovering the material forming said crystals, and
    stage (2) further lowering the temperature of said solution and repeating the procedure of stage (1) whereby crystals having a lower crystallization temperature than those formed in stage (1) are formed and collected on said at least one filter surface.

2. The method of claim 1, wherein the separation of the crystals is carried out in a fractionating column.

3. The method of claim 2, wherein the separated crystals are washed with cold solvent.

4. The method of claim 2, wherein the separated crystals are removed with hot solvent.

5. The method of claim 3, wherein the separated crystals are removed with hot solvent.

6. The method of claim 3, wherein after fractionation, the solvent is recovered from the fractions by distillation and reintroduced into the circuit.

7. The method of claim 3, wherein the solvent used for washing is stored in a tank and is fed to the circuit on a subsequent crystallization cycle.

8. The method of claim 1, wherein said mixture of materials is a mixture of fatty acid glycerides.

9. The method of claim 1, wherein said mixture of materials is palm oil.

10. The method of claim 1, wherein said solvent is a liquid alkane.

11. The method of claim 10, wherein said solvent is hexane.

12. The method of claim 9 or 11, wherein the run takes place for a short time at 20° C. and then the temperature is slowly and linearly lowered to minus 15° C. to form the crystals of the first fraction.

13. The method of claim 12, wherein the crystals are washed with solvent at about minus 15° C.

14. The method of claim 13, wherein the temperature is lowered from about minus 15° C. to about minus 24° C. to form crystals of a second fraction.

15. The method of claim 14, wherein the crystals of said second fraction are washed at about minus 24° C.

16. An apparatus for crystal fractionation of a mixture of materials dissolved in a solvent, said apparatus comprising in a circuit a circulation pump, a cooler, a heater, a storage tank and a fractionating column for separating the crystals from the circulated solution, said fractionating column comprising a plurality of filter surfaces located one above the other, said filter surfaces comprising spaced holes permitting a fluid flowing through or over the filter material to drop to the next lower filter surface, said holes of adjacent filter surfaces being off-set with respect to each other.

17. An apparatus as claimed in claim 16, wherein the cooler and the heater are a combined cooling/heating unit.

18. The apparatus of claim 16, wherein the filter surfaces are horizontally located.

19. The apparatus of claim 18, wherein the filter surfaces are mounted on spacer means being spaced from each other.

20. The apparatus of claim 16, wherein said fractionating column contains a distributor plate above the filter surfaces, and wherein said spacer means are tubes extending somewhat above the distributor plate.

21. The apparatus of claim 16, wherein each filter surface comprises a layer of a filter material and a support for said layer, said support having a flat sieve or perforated sheet surface.

22. The apparatus of claim 21, having a wire mesh on the upper surface of said layer.

23. The apparatus of claim 21, wherein said perforated sheet surface contains a plurality of closely spaced small holes, distributed substantially over its whole surface, and on said sheet, another layer having a plurality of holes being larger than said small holes.

24. The apparatus of claim 21, wherein said layer comprises a felt consisting of synthetic fibres.

25. The apparatus of claim 24, wherein the pores of the felt have a diameter of 10 to 100 microns.

26. The apparatus of claim 24, wherein the synthetic fibres are polypropylene.

27. The apparatus of claim 24, wherein the synthetic fibres are of polyester.

28. The apparatus of claim 16, wherein the fractionating column comprises slightly inclined filter surfaces connected for crosscurrent flow.

29. The apparatus of claim 28, characterized in that a distributing device is provided at the top of the fractionating column.

30. The apparatus of claim 16, wherein the fractionating column comprises at least one filter in the form of a vertically arranged archimedic screw.

31. The apparatus of claim 16, wherein at least one intermediary tank is provided to store the solvent used for washing and to feed it to the circuit on a consecutive fractionating.

32. The apparatus of claim 21, wherein said spacer means are tubes extending above said distributor plate 33. A method for fractionation of a mixture of materials dissolved in a solvent, said method comprising
    circulating and cooling the solution in a circuit, said circuit comprising a circulating pump, a cooler, a heater, a storage tank and a fractionation column, said fractionating column further comprising a plurality of filter surfaces located one above the other, said filter surfaces comprising spaced holes permitting a fluid flowing through or over the filter material to drop to the next lower filter surface, said holes of adjacent filter surfaces being off-set with respect to each other;

lowering the temperature gradually, causing formation of crystals suspended within said solution, said crystals forming while totally suspended within the solution; and continuously separating the crystals from the circulated solution fatty acid esters.

* * * * *

UNITED STATES PATENT AND TRADEMARK OFFICE
CERTIFICATE OF CORRECTION

PATENT NO. : 4,228,089

DATED : October 14, 1980

INVENTOR(S) : RUDOLF BISCHOF et al

It is certified that error appears in the above—identified patent and that said Letters Patent is hereby corrected as shown below:

Column 6, line 42: replace "has been" with ---was---.

Column 6, line 50: after "temperature", insert ---was---.

Column 8, line 63 (Claim 33): after "mixture of", insert ---fatty acid esters---.

Column 10, line 6: delete "fatty acid esters".

Signed and Sealed this

Twenty-fourth Day of March 1981

[SEAL]

Attest:

RENE D. TEGTMEYER

Attesting Officer     Acting Commissioner of Patents and Trademarks